United States Patent [19]
Gozes et al.

[11] Patent Number: 5,998,368
[45] Date of Patent: Dec. 7, 1999

[54] DERIVATIVES OF STRUCTURALLY MODIFIED VIP AND PHARMACEUTICAL COMPOSITIONS CONTAINING THEM

[75] Inventors: Illana Gozes, Ramat Hasharon; Matityahu Fridkin, Rehovot, both of Israel

[73] Assignees: Yeda Research and Development Co. Ltd., Rehovot; Ramot University Authority for Applied Research and Industrial Development Ltd., Tel-Aviv, both of Israel

[21] Appl. No.: 08/897,624

[22] Filed: Jul. 21, 1997

Related U.S. Application Data

[63] Continuation-in-part of application No. 08/412,986, Mar. 29, 1995, abandoned, which is a continuation-in-part of application No. 08/293,932, Aug. 22, 1994, abandoned, which is a continuation of application No. 07/969,444, Oct. 30, 1992, abandoned.

[30]     Foreign Application Priority Data

Oct. 31, 1991  [IL]  Israel .......................................... 99924

[51] Int. Cl.$^6$ .............................. A61K 38/00; C07K 5/00; C07K 7/00
[52] U.S. Cl. .............................. 514/12; 514/14; 530/313; 530/324; 530/327; 530/403
[58] Field of Search .................................... 530/324, 313, 530/327, 403; 514/12, 14

[56] References Cited

U.S. PATENT DOCUMENTS

| | | | |
|---|---|---|---|
| 3,879,371 | 4/1975 | Said et al. | 530/344 |
| 3,880,826 | 4/1975 | Said et al. | 530/324 |
| 4,016,258 | 4/1977 | Said et al. | 514/12 |
| 4,605,641 | 8/1986 | Bolin et al. | 514/12 |
| 4,732,892 | 3/1988 | Sarpotdar et al. | 514/178 |
| 4,734,400 | 3/1988 | Bolin et al. | 514/12 |
| 4,757,133 | 7/1988 | Ito et al. | 530/324 |
| 5,147,855 | 9/1992 | Gozes et al. | 514/12 |

FOREIGN PATENT DOCUMENTS

| | | |
|---|---|---|
| 0297068 | 12/1988 | European Pat. Off. . |
| 0354992 | 2/1990 | European Pat. Off. . |
| 0463450 | 1/1992 | European Pat. Off. . |

OTHER PUBLICATIONS

Werner, Haim et al., "High Levels of Vasoactive Intestinal Peptide in Human Milk," *Biochemical and Biophysical Research Communications*, vol.:133, No. 1, pp. 228–232, (1985).

Sachs, B.D., "Potency and Fertility: Hormonal and Mechanical Causes and Effects of Penile Actions in Rats," *Hormones and Behaviour in Higher Vertebrates*, pp. 86–110, (1983).

Merrifield, R.B., "Solid Phase Peptide Synthesis. I. The synthesis of a Tetrapeptide" *J. Am. Chem. Soc.*, vol. 85, pp. 2149–2154, (1963).

Okumura, Mutsuo et al, "Effect of Several Enhancers on the Skin Permeation of Water–Soluble Drugs," *Chem. Pharm. Bull.*, vol. 37, No. 5, pp. 1375–1378, (1989).

Gu, J. et al, "Decrease of Vasoactive Intestinal Polypeptide(VIP) in the Penises from Impotent Men," *The Lancet*, pp. 315–317, (1984).

Ottesen, Bent et al, "Penile Erection: possible role for vasoactive intestinal polypeptides as neuro–transmitter," *British Medical Journal*, vol. 288, pp. 9–11, (1984).

Dixson, A.F. et al, "Effects of tactile and electrical stimuli upon release of vasoactive intestinal polypeptide in the mammalian penis," *Journal of Endocrinology*, vol. 100, pp. 249–252, (1983).

Anderson, P–O et al, "Haemodynamics of pelvic nerve induced penile erection in the dog: possible mediation vasoactive intestinal polypeptide," *Journal of Physiology*, vol. 350, pp. 209–224, (1984).

Gozes, Illana et al, "Vasoactive Intestinal Peptide Potentiates Sexual Behavior: Inhibition by Novel Antagonist*," *Endocrinology*, vol. 125, No. 6, pp. 2945–2949, (1989).

Said, Sami I. et al, "Potent Peripheral and Splanchic Vasodilator Peptide from Normal Gut," *Nature*, vol. 225, pp. 863–864, (1970).

Rosenblatt, J. Biol. Chem., vol. 251, No. 1, pp. 159–164, 1976.

Gozes et al., J. Clinical Investigation, vol. 90, pp. 810–814 (1992).

Wagner, G. et al, "Intracavernosal injection of vasoactive intestinal polypeptide (VIP) does not induce erection in man per se.", World J. Urol., vol. 5, pp. 171–177 (1987).

Bodanzky et al, "The Vasoactive Intestinal Peptide (VIP) VI. The 27–Norleucine Analog of the Sequence 14–28", *Bioorganic Chemistry*, 3:320–323 (1974).

Wendleberger et al, "Total Synthesis of the 17–Norleucine Analogue of Porcine VII", pp. 290–295 (1980).

*Primary Examiner*—Avis M. Davenport
*Attorney, Agent, or Firm*—Browdy and Neimark

[57]     ABSTRACT

There are provided novel compounds for the treatment of male impotence. The compounds are derived from vasoactive intestinal peptide (VIP) in which the natural amino acid sequence is modified by replacement of any of the 5, 17 and 19 amino acid residues by other natural or non-natural amino acids, and they bear at least one terminal lipophilic group.

The modified VIP sequences are prepared by conventional peptide chain assembling methods.

The novel compounds and compositions containing them are suitable for transdermal application for treating male impotence.

19 Claims, 8 Drawing Sheets

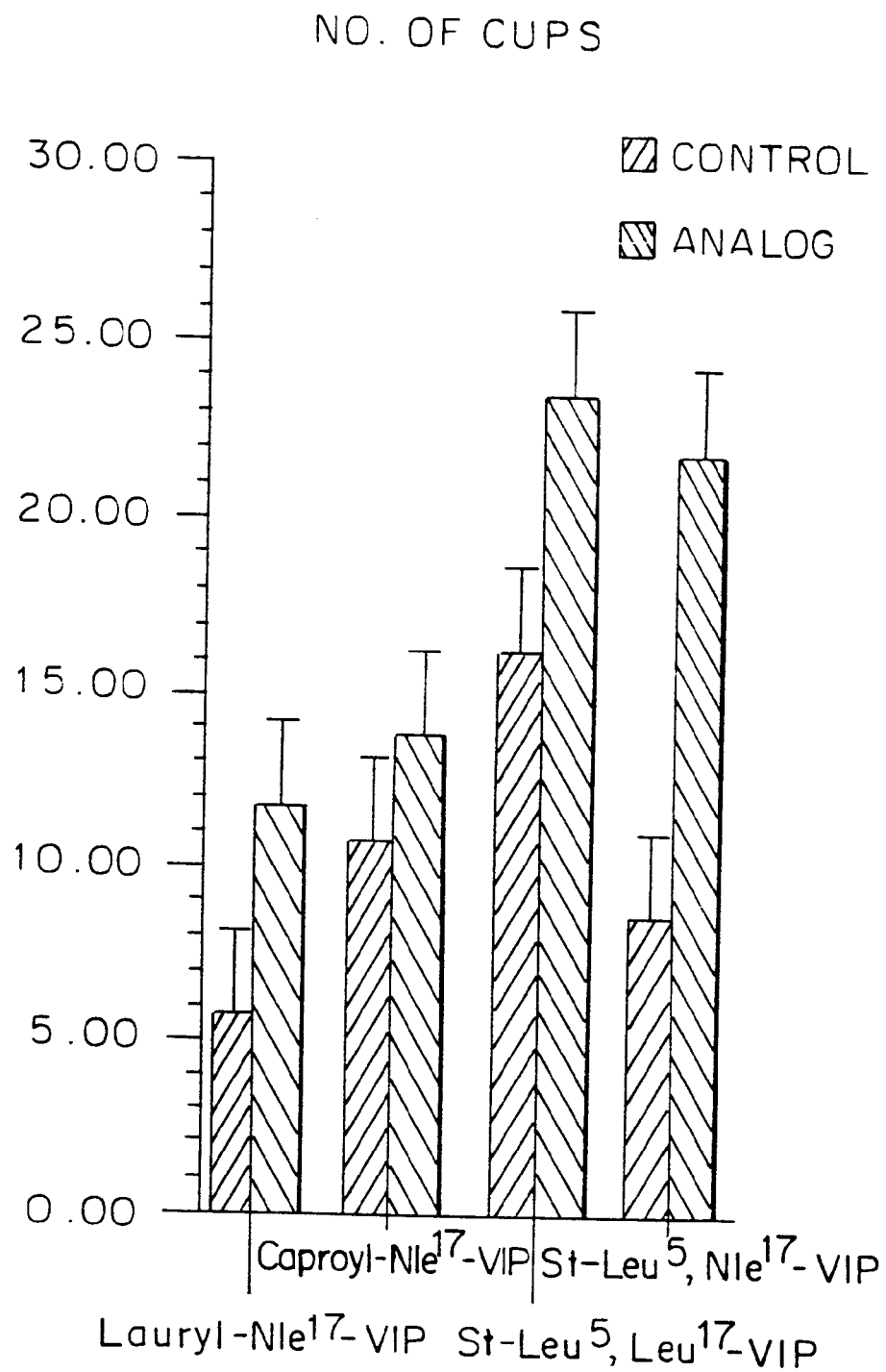

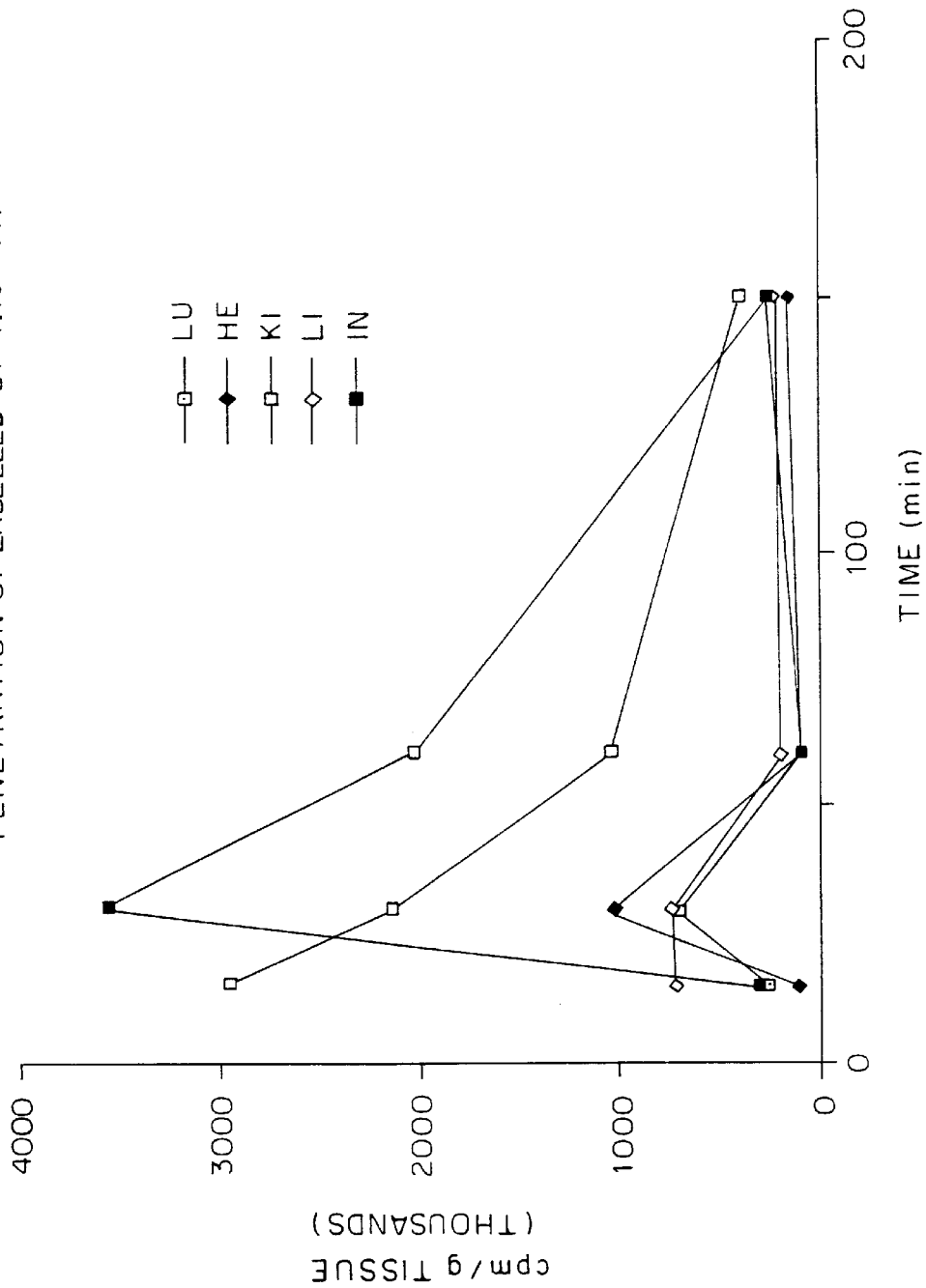

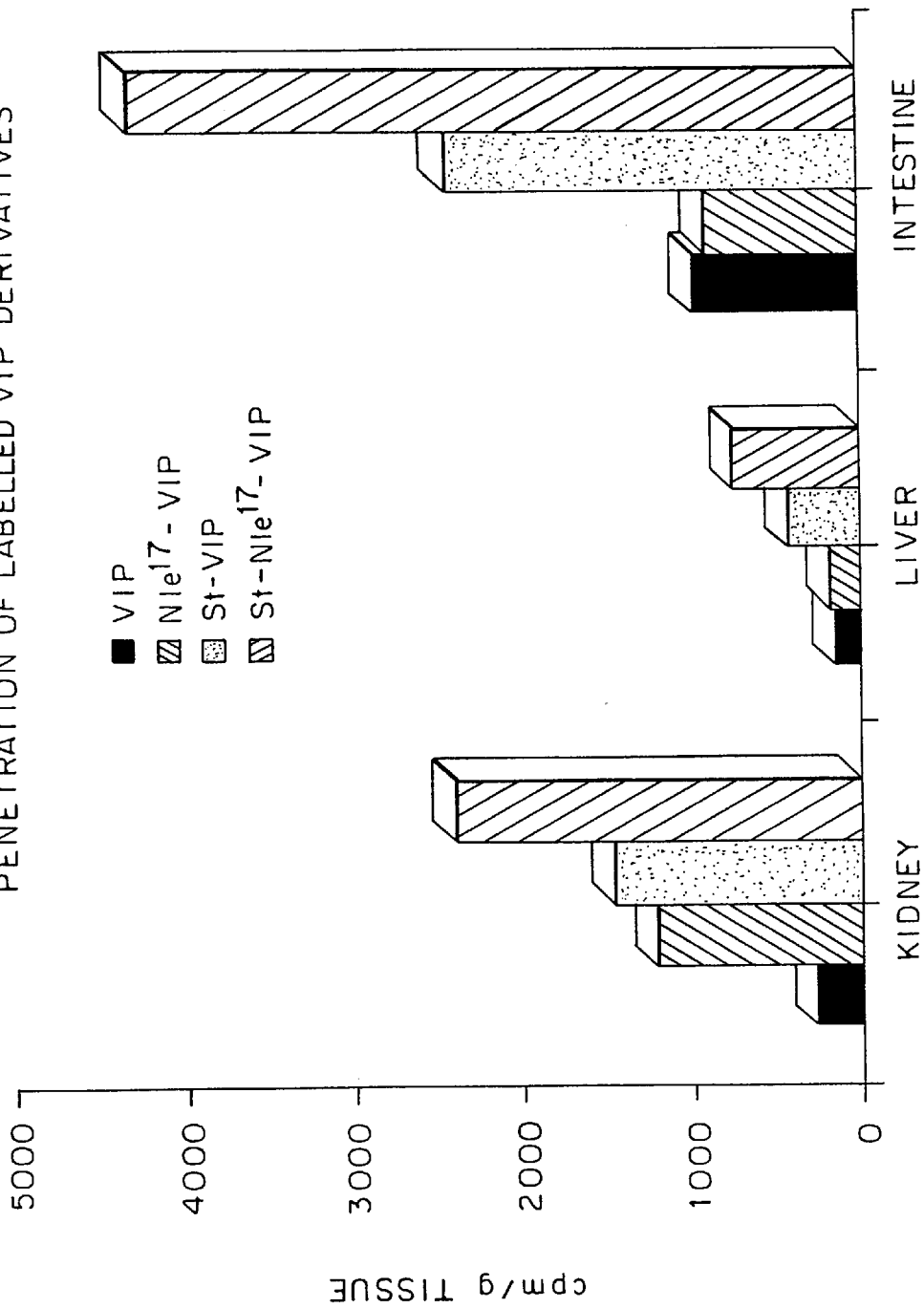

ically, it concerns the synthesis and transdermal
DERIVATIVES OF STRUCTURALLY MODIFIED VIP AND PHARMACEUTICAL COMPOSITIONS CONTAINING THEM This application is a continuation-in-part application of patent application Ser. No. 08/412,986 filed on Mar. 29, 1995, now abandoned which is a continuation-in-part application of patent application Ser. No. 08/293,932, filed Aug. 22, 1994, now abandoned which is a continuation application of patent application Ser. No. 07/969,444, filed Oct. 30, 1992, now abandoned.

FIELD OF THE INVENTION

The invention concerns novel derivatives of structurally modified vasoactive intestinal peptide (VIP), their pharmaceutical compositions and use in treating male impotence. More particularly, it concerns the synthesis and transdermal application of modified VIP conjugates which contain lipophilic end groups in suitable ointment compositions, to enhance sexual activity and penile erection.

REFERENCES

1. Said, S. and Mutt, V., *Nature* 225, 863 (1970).
2. Anderson, P. O. et al., *J. Physiol.* 350, 209 (1984).
3. Otteson, B, et al., *British Medical J.* 288, 9 (1984).
4. Dixon, A. F. et al., *J. Endocro.* 100, 249 (1984).
5. Gu, J. et al., *Lancet* 315 (1984).
6. Gozes, I. et al., *Endocrinology* 125, 2945 (1989).
7. EP-0 354 992 A2; U.S. Pat. No. 5,147,855.
8. Wagner, G. and Gerstenberg, T., *World J. Urol.* 5 171 (1987).
9. U.S. Pat. No. 4,605,641.
10. EP 297,068.
11. Merrifield, R. B., *J. Am. Chem. Soc.* 85, 2149 (1963).
12. Steuart, J. M. and Young, J. D., *Solid Phase Peptide Synthesis*, Pierce Chemical Corp., Rockford, Ill., 1984 (2nd edition).
13. Okumura, M. et al., *Chem. Pharm. Bull.* 37, 1375 (1989).
14. Sachs, B. D. in "Hormones and Behaviour in Higher Vertebrates" (Eds. Balthazart, J. Prove, E. and Gilles, R.) Springer-Verlag Berlin Heidelberg (1983) p. 86.
15. Werner, H. et al., Biochem. Biophys. Res. Commun. 133, 228 (1985).

BACKGROUND OF THE INVENTION AND PRIOR ART

Male impotence is a widespread syndrome affecting at least 10–15% of the human male population. It is estimated that in the United States alone, over ten million men suffer from varying degrees of impotence.

In principle, any man over the age of forty years may experience impotence occasionally due to neuroendocrine failures associated with ageing.

Impotence, which may bring suffering to the life of the afflicted individuals and those surrounding them, may be caused by both psychological or physiological problems. An additional problem associated with impotence is that often a suffering individual hesitates to seek medical help, especially in view of the limited convenient remedies available to the physician. Modes of treatment of impotence caused by organic reasons may involve surgery and implantation, as well as injection of smooth muscle relaxants such as papaverine or phenoxybenzamine.

Treatment of impotence with penile implants entails very serious disadvantages. The treatment requires surgery and results in a total and irreversible destruction of the erectile tissues of the penis precluding the ability of normal erection in the future.

Treatment of impotence with papaverine or phenoxybenzamine often results in priapism, a locking-up of an erection for a long period of time, typically a few hours and up to a period of twenty four hours. Apart from the embarrassment that priapism may cause, it is usually painful and may irreversibly damage erectile tissues. To be relieved, it may require in some cases pharmacological intervention. Even when priapism does not occur with the use of papaverine, such use is associated with a painful burning sensation in the first two minutes after injection, and there are indications that repeated use of papaverine causes extensive intracavernous fibrosis. In addition, phenoxybenzamine is suspected to be carcinogenic and therefore cannot be considered as a future effective drug for impotence In view of all the above, there is a need for a discreet, efficient and self-controlled treatment of impotence. The transdermal application of drugs seems to offer an attractive approach for such treatment, in view of the fact that such treatment is self-controlled and discreet and does not require any surgical intervention. The treatment using the drugs and pharmaceutical compositions according to the invention does not involve priapism.

The mechanism of penile erection requires the intactness of the endocrine system, the nervous systems and the vascular system. Vasoactive intestinal peptide (VIP) which was first isolated by S. Said and V. Mutt[1] and exhibits a wide range of physiological activities, was recently found to fulfil several criteria of a neurotransmitter mediating penile erection[2]. VIP was detected in fibres innervating cavernous smooth muscle. It was also elevated during erection[3,4] and decreased in impotent men[5]. Additionally, injection of exogenous VIP induced penile erection in man[3]. It was recently shown that systemic injection of VIP can stimulate sexual behaviour in rats with experimentally reduced masculine potential[6] and that lipophilic derivatives of VIP, and of the VIP$^{7-28}$ and VIP$^{16-28}$ fragments may be applied transdermally to enhance sexual behaviour[7]. In a study on normal subjects it was shown that injection of up to 20µg of VIP into the corpus cavernosum of a normal male, without subjecting the male to sexual stimulus, caused only slight swelling of the penis but not erection. However, when coupled with sexual stimulation, injection into the corpus cavernosum of as little as 1 µg of VIP facilitated full erection[8].

There are also known[9] VIP analogs in which some of the amino acids of the natural VIP sequence are replaced by others and in which the histidine in position 1, the so-called N-terminus, may optionally be acetylated. No enhancement of the sexual behaviour of males by such compounds was reported.

Dimaline et al.[10] disclose a VIP derivative wherein $X^2$ is Leu or Thr as an alternative amino acid to Met in the 17th position. However, they failed to suggest a modified molecule containing both an amino acid replacement and a covalently attached lipophilic, e.g. stearoyl residue. Moreover, such modification could result in an inactive analog due to enhancement of intramolecular hydrophobic interactions.

Japanese Kokai No, 4-59794 published on Feb. 26, 1992 describes an amidated homoserine derivative of modified VIP represented by L-leucine-17-VIP-HSe-NH$_2$ indicated for treatment of impotence and prevention of bronchial contraction by injection administration.

It is the object of the present invention to provide improved agents and compositions for the transdermal treatment of male impotence.

SUMMARY OF THE INVENTION

```
                                              (SEQ ID NO:1)
     1           5       7
H-His-Ser-Asp-Ala-Val-Phe-Thr-Asp-Asn-Tyr-Thr-Arg- 16   17      19
-Leu-Arg-Lys-Gln-Met-Ala-Val-Lys-Lys-Tyr-Leu-Asn-

28
-Ser-Ile-Leu-Asn-NH₂
```

The present invention is based on the surprising observation that VIP which was modified in at least one of positions, 5, 17 or 19, and is conjugated to at least one suitable lipophilic end group, at its N and/or C terminus, has a marked increased effectiveness in the treatment of male impotence by transdermal administration, as compared to native VIP bearing the same lipophilic end group or groups. Thus, for example, a relative minor change in the amino acid sequence of stearoyl VIP (St-VIP) induces an increase in the biological activity. It was further found quite generally that modified VIP with at least one lipophilic end group constitute very attractive drugs for treatment of male impotence. Moreover, an increase in tissue penetration has been assessed using radioactively labeled VIP and modified VIP bearing the same lipophilic end groups when applied transdermally in same amounts.

It has further been found that certain carriers can increase the effectiveness of tissue penetration making the pharmaceutical compositions of said structurally modified VIP into more effective drugs for the treatment of male impotence by way of transdermal application.

In accordance with the present invention, there is provided a novel substance being a conjugate of a lipophilic moiety and a modified vasoactive intestinal peptide (VIP) having the full sequence of formula I,

```
                    SEQ ID No. 2
                                              (SEQ ID NO:2)
     1                  7
R¹-His-Ser-Asp-Ala-X¹-Phe-Thr-Asp-Asn-Tyr-

16
Thr-Arg-Leu-Arg-Lys-Gln-X²-Ala-X³-Lys     I

28
Lys-Tyr-Leu-Asn-Ser-Ile-Leu-Asn-NH-R²
``` wherein
R¹ and R² are the same or different and are independently selected from the group consisting of: hydrogen, methyl, ethyl or a lipophilic group with the proviso that at least one of R¹ and R² is a lipophilic group; and X¹, X² and X³ are the same or different and each is a residue of a natural or non-natural amino acid, provided that when in full sequence both X¹ and X³ are valine, X² may not be methionine;
and a functional derivative of any such conjugate.

A "functional derivative" of a conjugate of the invention as described herein bears additional chemical moieties in at least one of the non-terminal amino acid residues of the peptidic portion of the conjugate, which moieties are not normally a part of said peptidic portion. These chemical moieties include, for example, ethers, esters and glycosides obtained by etherification, esterification and glycosylation, respectively, of a hydroxy side group of an amino acid such as serine, threonine and tyrosine; and esters and amides obtained by esterification and amidation, respectively, of the carboxy side group of aspartic acid. The additional chemical moieties can be introduced into the molecule by reacting the target amino acids, containing a hydroxy or carboxy side group, with the suitable organic derivatizing agent.

$X^1$, $X^2$ and $X^3$ may be any natural or synthetic amino acid, in a D- or L-form. Examples of preferred amino acids are isoleucine (Ile), tryptophan (Trp), alanine (Ala), glycin (Gly), leucine (Leu), phenylalanine (Phe), as well as valine (Val) and methionine (Met), and more preferably D- or L-norleucine (Nle). $X^1$, $X^2$ and $X^3$ may also be a non naturally occurring amino acid, for example α-aminobutyric acid (Abu).

Preferably, $X^1$ is selected from the group consisting of Val, Leu, Ala, Nle or Gly; $X^2$ is selected from the group consisting of D-Nle, L-Nle, Ile, Trp, Abu, Met, and Phe; and $X^3$ is selected from the group consisting of Val, Leu and Nle.

A "lipophilic group" as defined herein for $R^1$ and/or $R^2$ refers to a moiety which enhances the attraction of a molecule to organic solvents such as long chain aliphatic alcohols, dimethylsulfoxide and trifluoroethanol, The lipophilic moieties should preferably be devoid of charged or very polar functional groups such as ammonium, carboxyl and sulfonic groups, This definition includes, but is not limited to, the following species: (i) lipophilic aliphatic moieties comprising saturated or unsaturated, branched or linear aliphatic $C_3$–$C_{23}$ hydrocarbyl or acyl radicals such as propyl, hexyl, octyl, dodecyl, oleyl, octadecyl, tricosyl, propanoly, hexanoly (caproyl), octanoyl, dodecanoyl (lauroyl), oleoyl, octadecanoyl (stearoyl) and tricosanoyl (Tric; $CH_3$—$(CH_2)_{21}$—CO—), or such hydrocarbyl or acyl radicals substituted by one or more radicals selected from the group consisting of halogen, hydroxy, alkoxy, $NH_2$, $NR_2$, COOR, $CONH_2$ and $CONR_2$ wherein R is alkyl, such as for example aminocaproyl ($H_2N$—$(CH_2)_5CO$—) and carboxamidolauroyl ($H_2NCO$—$(CH_2)_{11}CO$—); and/or such hydrocarbyl or acyl radical interrupted by a heteroatom selected from O, S and/or N, such as for example the radical caproylaminolauroylamide [$(CH_2)_5CO$—NH—$(CH_2)_{11}CONH_2$]; (ii) lipophilic aromatic moieties comprising moieties consisting of one or more aryl or aroyl radicals, wherein aryl is phenyl, or naphthyl, examples of said radicals being phenyl, benzoyl, biphenyl and trityl, or of condensed rings such as naphthyl and naphthoyl, said arty radicals being optionally substituted by alkyl, alkoxy, halo and COOR; and (iii) lipophilic aromatic aliphatic moieties comprising both aromatic and aliphatic radicals as defined in (i) and (ii).

Preferred lipophilic moieties according to the invention are aliphatic acyl radicals, more preferably propanoyl, caproyl, lauroyl, stearoyl and tricosanoyl, and said radicals substituted by amino, e.g. aminocaproyl (Aca) or by carboxamido, e.g. carboxamido-lauroyl, or interrupted by an N atom, e.g. caproylaminolauroylamide, Several methods are known in the art for analysis of hydrophobicity-lipophilicity such as for example the partition of compounds between water and n-octanol, or by chromatography (e.g, HPLC, hydrophobic) employing lipophilic matrixes.

The artisan will appreciate the fact that there exists a large number of conjugates which fall under the definition of formula I and which differ from each other by the number, position and type of lipophilic groups, as well as by the number, position and types of amino acid modifications in at least one of positions 5, 17 and 19 of the native VIP. The artisan will further appreciate that some of the conjugates of formula I have a better physiological effect, in improving sexual functions, than others. In order to screen from among the large number of candidate compounds for those conjugates which are preferable for improving sexual function, the artisan should topically apply the candidate conjugates, together with a suitable vehicle, to the penis of a test animal and determine at least one of the following parameters:

i. latency to E2;
  ii. latency to cups;
  iii. number of E2; and
  iv. number of cups.

Determination of each of the above parameters may be carried out as specified in the detailed description of the invention. Those conjugates which cause an improvement in at least one of the above parameters as compared to control, are those which are suitable in accordance with the invention. Those compounds which cause a statistically significant improvement in one of the above parameters are preferable according to the invention. Those conjugates which cause a statistically significant improvement in both a cup parameter (latency to cup, or number of cups) and such improvement in an E2 parameter (latency to E2, or number of E2) are the most preferable conjugates in accordance with the invention.

Particularly preferred conjugates according to the invention are those of formula I in which the lipophilic moiety $R^1$ at the amino terminus is propanoyl, caproyl, lauroyl, stearoyl and tricosanoyl, and aminocaproyl and the radical $R^2$ at the carboxy terminus either hydrogen or carboxamidolauroyl or $R^1$ is hydrogen and $R^2$ is the lipophilic moiety caproylamino-lauroylamide, $X^2$ is Nle. Ile, Met or Trp, and $X^1$ and $X^3$ are each Val or Leu or $X^1$ is Ala or Gly.

The peptide chains of the novel compounds according to the invention are best prepared by solid phase synthesis$^{(11, 12)}$ and once these chains are assembled a terminal group $R^1$- and/or $R^2$- that is other than hydrogen is/are attached.

When $R^1$ and/or $R^2$ are acyl groups each or both terminal acyl groups may be introduced by conventional acylation procedures as described hereinafter in the Examples.

The conjugates of the invention wherein $R^1$ is hydrocarbyl are produced bar first preparing the peptidic moiety of the conjugate by known methods, removing the N-protecting group after incorporation of the last amino acid residue, reacting the amino-free peptide with the suitable aldehyde, reducing the resulting —CH=N— amine group to —CH$_2$NH— by methods known per se, and cleaving the final peptide-resin product by methods known per se, thus obtaining the desired conjugate of the invention wherein $R^1$ is hydrocarbyl.

The conjugates of the invention wherein $R^2$ is hydrocarbyl are prepared by peptide chain assembly on a Merrified resin (chloromethylated polystyrene) using Boc-Asp-β-cyclohexyl ester as a building block for Asp at position 8 of VIP, and upon completion of the peptide chain assembly, the ester group of the final peptide-resin product is cleaved by aminolysis with an amine of the formula $R^2$—NH$_2$, and deblocking of protecting groups and cleavage of the peptide from the resin are carried out by methods known per se, thus obtaining the desired conjugate of the invention wherein $R^2$ is hydrocarbyl.

Where, in the conjugates of the invention both $R^1$ and $R^2$ are hydrocarbyl, the $R^1$ radical is introduced by reaction with the suitable aldehyde while on the resin support as described above, followed by aminolysis with an amino of the formula $R^2$—NH$_2$, and deblocking of protecting groups and cleavage of the peptide from the resin by methods known per se, thus obtaining a desired conjugate wherein both $R^1$ and $R^3$ are hydrocarbyl.

In accordance with the present invention there are further provided pharmaceutical compositions for transdermal application for the treatment of impotence in male mammals comprising as active ingredient a compound of formula I above and a suitable pharmaceutically acceptable carrier.

The carrier is preferably selected from amongst those which enhance the tissue penetration of the active ingredient. Examples of suitable carriers are glycerine, lubricants, olive oil, nitroglycerin and Sefsol™, and mixtures thereof. Sefsol is a trademark (Nikko Chemicals. Tokyo) for glyceryl monocaprylate, propylene glycol didecanoate, propylene glycol dicaprylate, glyceryl tricaprylate and sorbitan monocaprylate and they are the preferred carriers in compositions according to the invention. Of these, glyceryl monocaprylate is particularly preferred.

The present invention further provides for the sustained release of a conjugate of the kind specified, a transdermal dispenser comprising an applicator loaded with said conjugate and adapted for application to the skin.

If desired, the conjugate in the applicator may be formulated into a pharmaceutical composition of the kind specified.

The new compounds according to the invention are useful in the treatment of male impotence, particularly by way of transdermal application. This way of treatment exhibits several advantages over the prior art. For one, it is non-surgical and does not entail tissue destruction. Moreover, it does not cause priapism or the burning pain associated with other drugs. Also the transdermal application is a much more discreet and convenient mode of application as compared to an intracavernosal injection. Furthermore, this method enables the use of a continuous slow release device which may enable spontaneous sexual activity without the need for a lengthy preparation, thus sparing an inflicted individual much of the usual embarrassment.

DESCRIPTION OF THE DRAWINGS

In the following specific description reference will be made to the annexed drawings in which:

FIG. 6 shows the number of cups of animals administered with: lauryl-Nle$^{17}$-VIP; caproyl-Nle$^{17}$-VIP, St-Leu$^5$-Leu$^{17}$-VIP and St-Leu$^5$-Nle$^{17}$-VIP as compared to control;

FIG. 7 shows distribution of radioactively labeled stearoyl-Nle$^{17}$-VIP in lungs (LU), hearts (HE), kidneys (KI), liver (LI) and intestines (IN) at different times following topical application; and FIG. 8 shows the amounts of radioactively labeled VIP, Nle$^{17}$-VIP, St-VIP and St-Nle$^{17}$-VIP which penetrated the kidney, liver and intestines 30 mins. after topical application.

DESCRIPTION OF SPECIFIC EMBODIMENTS

Figure 1:
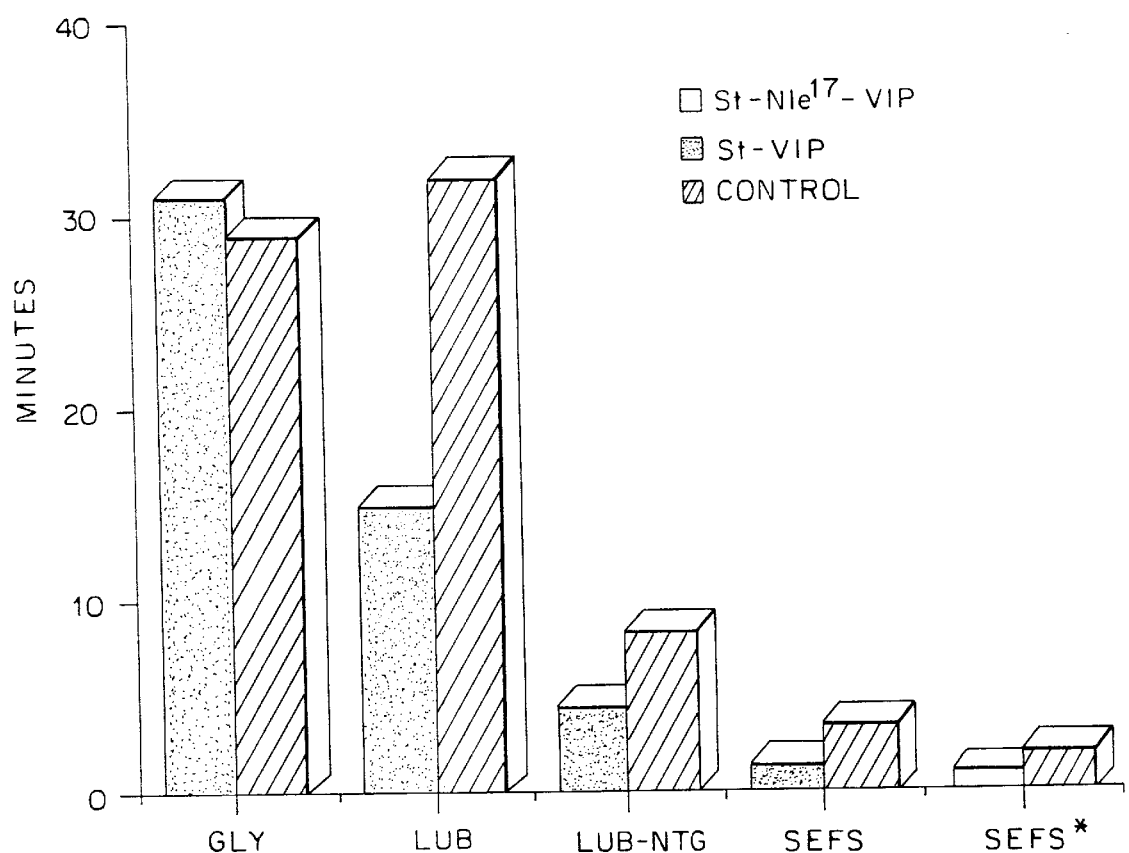
FIG. 1 shows the latency to first E2 (min) of animals topically administered with various vehicles containing St-Nle$^{17}$-VIP, St-VIP and vehicle alone (control)

The following examples illustrate the various aspects of the present invention, it being understood that the invention is not limited thereto.

EXAMPLE 1

Synthesis of Stearoyl-Nle$^{17}$-VIP

The synthesis of the said novel modified VIP conjugates will be illustrated by the synthesis of the most preferred compound according to the invention, i.e. stearoyl-norleucine$^{17}$-VIP (St-Nle$^{17}$-VIP).

A peptide chain was assembled manually, in a mechanical shaker. according to the general principles of the solid-phase methodology of Merrifield[10,11] on a methyl benzhydryl amine resin (MBHA), purchased from Nova, Switzerland. All solvents, methylene chloride ($CH_2Cl_2$), N-methylpyrrolidone (NMP), and dimethyl sulfoxide (DMSO) were analytical products of Merck, Germany. Trifluoroacetic acid (TFA), diisopropylethylamine (DIEA) and N,N'-dicyclohexylcarbodiimide (DCC) were purchased from Aldrich, U.S.A. 1-Hydroxybenzotriazole (HOBT) was obtained from Nova, Switzerland. All protected amino acid derivatives (Boc-AA) were of the L-configuration and were obtained from Bachem, Switzerland. N$^\alpha$-amino acid functions were protected, throughout the synthesis, by the t-butyloxycarbonyl (t-Boc) group. Side chain functions were protected as follows: Sir, Asp, Thr with benzyl; Lys with 2-chlorobenzyloxycarbonyl; Tyr with 2,6-dichlorobenzyl; His with benzyloxycarbonyl, and Arg with p-toluenesulfonyl.

The synthesis was initiated by coupling of Boc-Asn (0.46 g; 2 mmol) to the methylbenzhydryl amine resin (1 g) using DCC (0.42 g; 2 mmol) and HOBT (0.272 g; 2 mmol) as agents. Loading (0.39 mmol/g) was determined by amino acid analysis. Unreacted residual amino groups on the polymer were capped by reacting with acetic anhydride and triethylamine (1 ml and 0,5 ml, correspondingly) in $CH_2Cl_2$ (10 ml). The peptide chain assembly was started with Boc-Asn-MBHA resin, following the protocol outlined in Table 1.

TABLE 1

| | Solid Phase Peptide Synthesis | |
|---|---|---|
| Step | Reagent/Solvents | Time (min.) |
| 1 | TFA in $CH_2Cl_2$ (30% v/v) | 3 |
| 2 | TFA in $CH_2Cl_2$ (50% v/v) | 17 |
| 3 | $CH_2Cl_2$ | 5 × 2 |
| 4 | 5% DIEA in $CH_2Cl_2$ (v/v) | 5 |
| 5 | 5% DIEA in NMP (v/v) | 2 |
| 6 | NMP | 5 × 2 |
| 7 | Ninhydrin test | |
| 8 | 1.6 mmol Boc A.A + 1.6 ml 1N HOBT + 1.6 ml 1N DCC all in NMP; preactivation −30 min; filter and add solution to polymer (1 g) DMSO (final vol. 20% v/v) | 45<br>20 |
| 9 | DIEA - (6 mmol in NMP) | 10 |
| 10 | NMP | 5 |
| 11 | $CH_2Cl_2$ | 3× 2 |
| 12 | Ninhydrin test | |
| 13 | 10% $Ac_2O$ + 5% DIEA in $CH_2Cl_2$ | 5 |

TABLE 1-continued

| | Solid Phase Peptide Synthesis | |
|---|---|---|
| Step | Reagent/Solvents | Time (min.) |
| 14 | 10% $Ac_2O$ in $CH_2Cl_2$ | 15 |
| 15 | $CH_2Cl_2$ | 3 × 2 |

Solvents for all Washings and reactions were measured to volumes of 10 ml/g resin. All couplings were performed using HOBT active esters of Boc-amino acid derivatives prepared by DCC prior to each coupling step. A molar ratio of 4:1 of Boc-amino acid 1-hydroxybenzotriazole ester (Boc-AA-OBT) and $\alpha$-amino group of growing peptide chain, respectively. was employed for couplings. Coupling reactions were monitored by boiling a few mg (about 3) of polymer in a solution of ninhydrin in pyridine-water for 2 min. Coupling of Boc amino acids was repeated twice to ensure complete reaction. In the second coupling, half of the amount of Boc-AA-OBT was used. As a rule, after completion of each coupling step,. residual amine groups were capped by treating the resin with acetic anhydride (10%) and diisopropylethylamine (5%) in methylene chloride.

Following completion of the peptide chain assembly, the t-Boc protecting group of His was removed, as usual, by 50% TFA in $CH_2Cl_2$ and the newly free $\alpha$-amino group was coupled to stearic acid (0.56 g; 2 mmol) using DCC (0.42 g; 2 mmol) and HOBT (0.27 g, 2 mmol) as reagents. The reaction proceeded for 45 min and was repeated twice. The fully assembled peptide-resin was washed with $CH_2Cl_2$ according to protocol, and then dried under vacuum overnight, over $P_2O_5$. Deblocking of protecting groups and cleavage of the peptide from resin was achieved by the anhydrous HF technique. Thus, the peptide-resin (1 g) was treated in a Teflon™ HF apparatus (Multiple Peptide System) with 9 ml HF in the presence of a mixture of 1.5 ml of p-thiocresol and p-cresol (1:1, v/v) for 1 hr at 0° C. The HF was removed by vacuum and the resin treated with peroxide-free ether, filtered, washed with other, dried and extracted with 50% acetic acid in water (3×75 ml). Lyophilization of aqueous filtrate yielded the crude stearoyl-Nle$^{17}$-VIP (400–500 mg).

The crude product was dissolved in 50% aqueous acetic acid and passed through a Sephadex G-25 column (75×2 cmi) employing 0.1N acetic acid as an eluent. Elution was monitored spectrophotometrically at 274 nm. The first emerging peak was collected. Lyophilization of the aqueous solution yielded the peptide free of the aromatic additives added as scavengers at the HF-cleavage step. Yield was 50–70%.

Purification by high performance liquid chromatography (HPLC) was carried out on the Sephadex-fractionated products. It can be performed, however, on the crude peptide. Purifications were achieved on Merck RP-8 column (7 $\mu$M; 250×25 mm). The peptide was applied in 10% acetonitrile in water and eluted with a linear gradient established between 0.1% TFA in water and 0.1% TFA in 75% acetonitrile in water at a flow rate of 5 ml/min. Fractions were collected and cuts made after inspection by analytical HPLC. Derived fractions were pooled and lyophilized. Yield of the pure peptide was 30–35%.

Purity of product was ascertained by analytical HPLC (Merck RP-8, 125×10 mm column) and amino acid analysis, following exhaustive acid hydrolysis (6N HCl), which gave the expected values of each constituent amino acid.

The stearoyl-Nle$^{17}$-VIP is more stable than the stearoyl-VIP in which the amino acid sequence was not altered, Other lipophilic derivatives are coupled to Nle$^{17}$-VIP by the same process in which after removing the t-Boc protecting group of His, the newly free α-amino group is coupled to the suitable carboxylic acid using DCC and HOBT as described above.

EXAMPLE 2

Synthesis of Stearoyl-Nle$^{17}$-VIP

In all alternative method, synthesis of St-Nle$^{17}$-VIP was performed as follows:

The peptide chain was assembled manually in a mechanical shaker according to the general principles of the solid-phase methodology of Merrifield on a 4 resin, purchased from Nova, Switzerland. All solvents: methylene chloride ($CH_2Cl_2$), N-methylpyrrolidone (NMP), and dimethyl formamide (DMF) were analytical products of Merck, Germany. Trifluoroacetic acid (TFA), diisopropylethylamine (DIEA) and N,N'-dicyclohexylcarbodiimide (DCC) were purchased from Aldrich, U.S.A. 1-Hydroxybenzotriazole (HOBT) was obtained from Nova, Switzerland. All protected amino acid derivatives (FMOC-AA) were of the L-configuration and were obtained from Bachem, Switzerland. N$^α$-amino acid functions were protected throughout the synthesis by the fluorenylmethoxycarbonyl (FMOC) group Side chain functions were protected as follows: Ser, Asp, Thr with t-butyl; Lys with t-butyloxycarbonyl; His with benzyloxymethyl (BOM); and Arg with methoxytrimethylphenylsulfonyl (Mtr).

The synthesis was initiated by removal of the FMOC-group, from the commercial polymer: 4-(2',4'-dimethoxyphenyl-FMOC-aminoethyl)-phenoxy resin (0.47 mmol of amino group/g), according to steps 1 and 2 (see protocol). 10 g of polymer, contained in 2 reaction vessels, were employed. The volume of solvents used was 20–25 ml in each vessel. Assembly of the peptide chain was initiated by coupling FMOC-Asn (1.41 g, 4 mmol) to the resin (5 g) using DCC (0.84 g, 4 mmol) and HOBT (0–55 g, 4 mmol) agents. The coupling was repealed. Loading (0.39 mmol/g) was determined by amino acid analysis. Unreacted residual amino groups on the polymer were capped by reacting with acetic anhydride (10%) and diisopropylethylamine (5%) in $CH_2Cl_2$. The peptide, chain assembly was started from the FMOC-Asn-resin, following the protocol outlined in Table 2.

TABLE 2

Solid Phase Peptide Synthesis

| Step | Reagents | min. |
| --- | --- | --- |
| 1 | 10% piperidine/DMF | 5 |
| 2 | 20% piperidine/DMF | 15 |
| 3 | DMF | 2 |
| 4 | DMF | 2 |
| 5 | DMF | 2 |
| 6 | $CH_2Cl_2$ | 2 |
| 7 | $CH_2Cl_2$ | 2 |
| 8 | NMP | 2 |
| 9 | Ninhydrin test | |
| 10 | FMOC-amino acid/HOBT/DCC (molar ratio 1:1:1 in NMP preactivation) | 120 |
| 11 | DMF | 2 × 2 |
| 12 | $CH_2Cl_2$ | 2 |
| 13 | $CH_2Cl_2$ | 2 |
| 14 | $CH_2Cl_2$ | 2 |

TABLE 2-continued

Solid Phase Peptide Synthesis

| Step | Reagents | min. |
| --- | --- | --- |
| 15 | Ninhydrin test | |
| 16 | 10% $Ac_2O$ + 5% DIEA in $CH_2Cl_2$ | 3 |
| 17 | 10% $Ac_2O$ in $CH_2Cl_2$ | 5 |
| 18 | $CH_2Cl_2$ | 2 |
| 19 | $CH_2Cl_2$ | 2 |
| 20 | $CH_2Cl_2$ | 2 |
| 21 | DMF | 2 |

Solvents for all washings and reactions were measured to volumes of 10 ml/g resin, except for coupling (step 10) when volumes of about 5 ml/g resin were employed. All couplings were performed using HOBT active esters of FMOC-amino acid derivatives, prepared by DCC prior to each coupling step. A molar ratio of 2;1 of FMOC-amino acid 1-hydroxybenzotriazole ester (FMOC-AA-OBT) and a-amino group of growing peptide chain, respectively, was employed for couplings. Coupling reactions were monitored by boiling a few mg (about 3) of polymer in a solution of ninhydrin in pyridine-water for 2 min. Coupling of FMOC-amino acids was repeated twice or more to ensure complete reaction. In the second, and when necessary other, couplings, half of the amount of FMOC-AA-OBT was used. Proceeding steps, aimed at addition of the next amino acid were initiated only after a negative ninhydrin test (step 15; see protocol). As a rule, after completion of each coupling step, residual amine groups were capped by treating the resin with acetic anhydride (10%) and diisopropylethylamine (5%) in methylene chloride, Following completion of the peptide chain assembly, the FMOC protecting group of His was removed, as usual, by piperidine in DMF and the newly free α-amino group was coupled (in each reaction vessel) to stearic acid (1.12 g, 4 mmol) using DCC (0.84 g, 4 mmol) and HOBT ((0.54 g, 4 mmol) as reagents. The reaction proceeded for 120 min and was repeated twice. The resin containing the fully assembled peptide-chain was washed with $CH_2Cl_2$ according to protocol, and then dried under vacuum overnight, over $P_2O_5$. Deblockiing of protecting groups and cleavage of the peptide from resin was achieved as follows: 1 g of dried resin was placed in a 100 cc flask to which thioanisole (2 ml) and ethanedithiol (2 ml) were added. The mixture was cooled to 4° C. in an ice bath and 20 ml of trifluoroacetic acid added, and 5 min later trifluoromethanesulfonic acid (2 ml) was also added. The mixture was gently stirred at room temperature for 50 min.

The reaction mixture was then cooled to 4° C. and poured into 500 ml of dry ether. After stirring for 60 min at 4° C., the solid material (resin and peptide) was filtered on a scinter funnel, washed with dry ether,. dried and then extracted with 50% aqueous acetic acid (100 ml). The solution obtained, containing the peptide, was concentrated in high vacuum and the residue (about 15 ml) was directly loaded on a Sephadex G25 column (45×6 cm). The column was eluted with 0.1N acetic acid at a flow rate of 45 ml/1 hr. Elution was monitored at 274 nm, Lyophilization of the aqueous solution, containing the desired fraction, yielded the peptide free of the aromatic additives added as scavengers at the acidolytic cleavage step. Yield was about 400 mg of a white powder.

The material showed the required amino acid content and ratio as revealed by amino acid analysis following exhaustive acid hydrolysis.

Further purification by high performance liquid chromatography (HPLC) was carried out on the Sephadex-fractionated products. It can be performed, however, on the crude peptide. Purifications were achieved on Merck RP-8 column (7 $\mu$M, 250×25 mm column). The peptide was applied in 35% acetonitrile in water and eluted with a linear gradient established between 35% acetonitrile and 0.1% TFA in water and 0.1% TFA in 75% acetonitrile in water at a flow rate of 10 ml/min. Fractions were collected and cuts made after inspection by analytical HPLC. Derived fractions were pooled and lyophilized. Yield of the pure peptide was 30–35%. Other peptides described hereinafter were synthesized using the same process at similar yields.

EXAMPLE 3

Synthesis of Caproyl and Lauroyl-Nle$^{17}$-VIP

These two lipophilic derivatives of Nle$^{17}$-VIP were synthesized exactly as described in Example 2, i.e. the preparation of St-Nle$^{17}$-VIP, with one change. In the last coupling step, either caproic acid or lauric acid, respectively, were attached to the free $\alpha$-amino terminal group of His$^1$, instead of stearic acid. Removal of the products from the polymeric carrier, along with side-chain deprotection, and purification of the crude products where exactly as described in Example 2. Yields of the pure peptides were similar, i.e. 30–35% and even higher.

The two peptides were eluted from the HPLC-column (Merck RP-8; 7 $\mu$M, 250×25 mm) earlier than St-Nle$^{17}$-VIP. Thus, when a linear gradient was established between 30% acetonitrile and 0.1% TFA in water (A) and 0.1% TFA in 75% acetonitrile in water (B) (at a flow-rate of ml/min), during 50 min, St-Nle$^{17}$-VIP, caproyl-Nle$^{17}$-VIP and lauroyl-Nle$^{17}$-VIP were eluted with 85%, 50% and 65% of eluent B. Purity of the product was ascertained by amino acid analysis and mass spectrometry.

EXAMPLE 4

Peptide Synthesis Via Automatic Procedure

Syntheses of St-Nle$^{17}$-VIP, caproyl-Nle$^{17}$-VIP and lauroyl-Nle$^7$-VIP, as well as all other lipophilic-VIP and modified-VIP derivatives shown in Table 3, were also achieved by automatic procedure employing an ABIMED AMS 422 synthesizer (ABIMED, Langenfeld, Germany) using the commercially available protocols via the Fmoc-strategy. All protected amino acid derivatives were as previously outlined for the manual Fmoc-procedure with one exception, i.e. Fmoc-Arg(PMC), (PMC=2, 2, 5, 7, 8-pentamethylchromnan-6-sulphonyl), replaced Fmoc-Arg (Mtr). PyBOP, i.e. benzotriazolyl-N-oxy-tris (dimethylamino)phosphonium hexafluorophosphate, was used as a coupling agent. Peptide chains were assembled as in Example 2, on a 4-([2',4'-dimethoxyphenyl]-Fmoc-aminoethyl)phenoxy resin (Rink Amide Resin, Nova, Switzerland).

Final cleavage of the peptide chain from the resin along with side chain deprotection was achieved as follows: cleavage mixture; 90% TFA, 5% water, 5% triethylsilane. The resin, 100 mg, loaded with peptide was incubated for 30 min, with a 3 ml cleavage mixture inside the reaction column used for solid phase synthesis. After 30 min, the reaction mixture was separated from the cleaved resin and cleavage continued for an additional 3 hrs. The cleaved peptide was precipitated with ice cold tert-butylmethyl ether and centrifuged (4° C., 2000 rpm). The solution was decanted and the pellet was; dissolved in water and frozen for lyophilization to yield a white powder. Purification of the crude peptides was performed as described above. Yields were 30–45%.

The following stearoyl analogs of VIP were also prepared employing the methodology of Examples 3 and 4:

St-Leu$^5$-Nle$^{17}$-VIP
St-Leu$^{17}$-VIP
St-Leu$^5$,Leu$^{17}$-VIP
St-Thr$^5$-VIP
St-Val$^{17}$-VIP

Purity of the products was ascertained by analytical HPLC as for stearoyl-Nle$^{17}$-VIP above and amino acid analysis, giving the expected values of each constituent amino acid.

EXAMPLE 5

Preparation of R$^1$-Nle$^{17}$-VIP Wherein R$^1$ is Hycrocarbyl

The peptide chain is assembled on the polymeric support, methyl benzhydryl amine resin (MBHA), (containing 0.39 mmol Asn/1 gr) as described in Example 1. After incorporation of the last amino acid residue (histidine) the N-$\alpha$-protecting group (t-Boc) is removed by TFA, the polymer is treated with DIEA, washed and ninhydrin tested. The polymer is then suspended in ethyl alcohol (1 gr/10 ml) and the corresponding aldehyde R$^1$—CH=O is added (3–4 equivalents of aldehyde to 1 equivalent of free N-terminal amino group) and the mixture is gently agitated overnight at room temperature. The polymer is filtered, washed with ethanol (3×10 ml), resuspended in ethanol and NaBH$_4$ (3–4 equivalents of reducing agent to 1 equivalent of Schiff base; R$^1$—CH=N—His—) and the mixture is gently agitated for 2 hr at room temperature. Alternatively. NaBH$_3$CN (3–4 equivalents to 1 equivalent of Schiff base) can be employed (in the presence of 0.1–0.2 ml of acetic acid). Condensation and reduction reactions can also be performed in other organic solvents, such as DMF or NMP. Following completion of reduction, the polymer is filtered, washed and dried, and treated with HF as described for stearoyl-Nle$^{17}$-VIP. The crude product is purified in the same manner as described in Example 1, to afford the desired final products.

Purity of the product was ascertained by analytical HPLC (Merck RP-8, 125×4 mm column) and amino acid analysis, following exhaustive acid hydrolysis (6N HCl), which gave the expected values of each constituent amino acid.

EXAMPLE 6

Preparation of R$^1$-NH-Nle$^{17}$-VIP-NH-R$^2$ where R$^2$ is hydrocarbyl

The first amino acid, Boc-Asn, was attached to 1% crosslinked chloromethylated polystyrene (Chemalog, South Plainfield, N.J., U.S.A.) as follows: triethylamine (4.75 mmol; 0.66 ml) was added to the amino acid derivative (5 mmole; 1.16 gr) in absolute ethanol (35 ml), and the mixture was allowed to stand for 5 min at room temperature. The polymer (5 gr) was then added and the mixture was gently refluxed for 60 h at 78° C. Alternatively, 5 mmol of Boc-Asn was dissolved in a mixture of EtOH (12 ml) and water (3 ml), and the pH adjusted to 7.5 with a 20% aqueous solution of CSCO$_3$. The solution was flash evaporated three times with benzene and the residue dried over P$_2$O$_5$ in a dessicator for 5 h. DMF (30 ml) was then added to dissolve the material, followed by 5 gr of polymer and the mixture was stirred for 36 h at 50° C. Loading (0.4 mmol/gr) was determined by amino acid analysis.

Peptide chain assembly was performed as in Example 1. However, Boc-Asp (β-cyclohexyl ester) was used instead of Boc-Asp (β-benzyl ester) as a building block for Asp at position 8. The cyclohexyl group is stable toward aminolysis. On completion of the desired peptide chain assembly, the polymer is washed and dried as above. The peptide-resin ester product is then suspended in absolute ethanol, or a 1:1 v/v mixture of EtOH, and DMF (1 gr/10 ml) and the desired amine ($R^2$—$NH_2$; mmol) is then added and the mixture is gently stirred at room temperature for 48 h. TLC, using the solvent system N-butanol:acetic acid:$H_2O$; pyridine (15:3:12:10 v/v), revealed the appearance of a product which was detached from the polymeric support. The polymer was extracted with ethanol (3×10 ml), DMF (3×10 ml) and the solvents were evaporated in high vacuum and the oily, semi-solid, residue was then treated, as above, with HF to remove side-chain protecting groups. The crude products were purified in the same manner and comparative yields as described for stearoyl-Nle$^{17}$-VIP, to afford the desired final products.

EXAMPLE 7

Ointment Compositions

The following ointment compositions were prepared and tested for transdermal application of lipophilic conjugated modified VIP derivatives in accordance with the present invention. Similar conjugates of unmodified VIP derivatives were tested for comparison.

1. Ointment containing glycerine as a carrier:
    The ointment was prepared as follows; 2 g glycerine+ 10 mg stearoyl-VIP+7 drops of DMSO (dimethylsulfoxide). Each rat received 30–50 μg of stearoyl-VIP in about 10 μl ointment. (GLY in FIG. 1).
2. Ointment containing lubricant as a carrier.
    The ointment was prepared as above, only glycerine was replaced bad lubricant (K-Y Lubricating Jelly), Johnson & Johnson, containing propylene glycol and glycerine), 7 drops of DMSO equals about 130 μl. (LUB in FIG. 1).
3. Ointment containing lubricant and nitroglycerine as a carrier:
    Prepared as in (2) above with 1.7 ml nitroglycerine (1 mg/ml), (LUB-NTG in FIG. 1).
4. Ointment containing Sefsol 318™$^{(13)}$ as a carrier:
    (a) The ointment composition was: 31.2 μl 10% Sefsol 318™ (glyceryl monocaprylate), and either 0.24 mg stearoyl-VIP in 31.2 μl DMSO (1–2μl per animal) (SEFS in FIG. 1) or 0.24 rig stearoyl-Nle$^{17}$-VIP in the above (SEFS* in FIG. 1).
    (b) For other analogs described hereinafter 10 μl of solution were used per animal containing 7 μg of active material in a vehicle containing 5% Sefsol and 20% isopropanol.

EXAMPLE 8

Biological Tests for Penile Reflexes

The biological tests involved measurements of penile reflexes in castrated rats following transdermal application of modified VIP conjugates, In a first type of biological experiment the effects of compositions of stearoyl-VIP with various carriers on penile reflexes were measured and it was found that Sefsol was the most effective carrier. In a further set of experiments the effects of stearoyl-VIP compounded with Sefsol 318™ were compared with those of stearoyl-Nle$^{17}$-VIP compounded with Sefsol 318™.

In a second type of biological experiments the effects of compositions containing other modified VIP conjugates compounded with Sefsol 318™ were tested.

In a third type of biological experiments the distribution in various organs of several radioactively labeled modified VIP conjugates was monitored.

(a) Methods

Animal model for impotence.

Rats with reduced sexual potential due to castration were employed. Male rats (250–300 g, about three month old) were kept in a 12-hours light, 12-hours dark cycle. Experiments were always conducted within the dark period, 2–6 hours after the onset of darkness. Male rats were castrated and given partial testosterone replacement (4 μg/100 g body weight) in the form of daily injection for 14–21 consecutive days (the duration of the experiment). Experiments were conducted one week following surgery.

Direct evaluation of penile reflexes (erections)

A procedure was utilized that employed the technique that measures sexual reflexes in the penis, which enables direct evaluation of penile erection following transdermal administration of the drug. Successful reproduction depends, in large part, upon the precise execution of temporally organized, functionally related behavioural units. In these experiments, we concentrated on the final stages of the erection process (reddening of the penis accompanied by its distension and extension leading to complete erection) and monitored the latency time to the first E2 and first cup$^{(14)}$.

For testing, each animal was restrained in a supine position with the anterior portion of its body enclosed in a loosely fitting cylinder (7 cm diam). After a belt was secured around the torso, the glans penis was extruded from its sheath and gently held perpendicular to the abdomen by a thin wooden applicator positioned at the posterior of the penis. The legs of the male were held by the observer and this position was maintained throughout the test period. The duration of the session was 45 minutes. The latencies and numbers of E2 and cups were recorded and plotted.

An E2 is defined as a complete erection which can be followed by cup in which the penile tip is turned into a cup-like structure, whereby the glands flare out such that the penis is wider in its distal portion than its base. This final stage requires E2 and is probably a pre-requisite for ejaculation (13). Using, all the parameters one can obtain a reliable measure of the sexual activity of the tested rat.

(b) Results

The effect of topical application of different ointment compositions comprising:

stearoyl-VIP (St-VIP)
stearoyl-Nle$^{17}$-VIP (St-Nle$^{17}$-VIP)
stearoyl-Leu$^5$-Leu$^{17}$-VIP
lauroyl-Nle$^{17}$-VIP
caproyl-Nle$^{17}$-VIP on penile reflexes is shown in FIGS. 1A to 1F, Six to ten animals were tested in this paradigm for each variable. Control animals received ointment compositions without the modified VIP conjugate.

Latency to first E2 (St-Nle$^{17}$-VIP)

FIG. 1 shows the latency to first E2 of animals administered with different vehicles comprising St-VIP, St-Nle$^{17}$-VIP and vehicle alone (control). The different vehicles used were: glycerol (GLY), lubricate (LUB), lubricate and nitroglycerine (LUB+NTG), Sefsol 318™ either with St-VIP (SEFS) or with St-Nle$^{17}$-VIP (SEFS*). As can be seen the shortest latency to first E2 is observed when using the composition comprising St-Nle$^{17}$-VIP in Sefsol 318™ (SEFS* in lane 5), The E2 latency for this composition is about 1 minute.

Latency to first cup (St-Nle$^{17}$-VIP)

Figure 2:
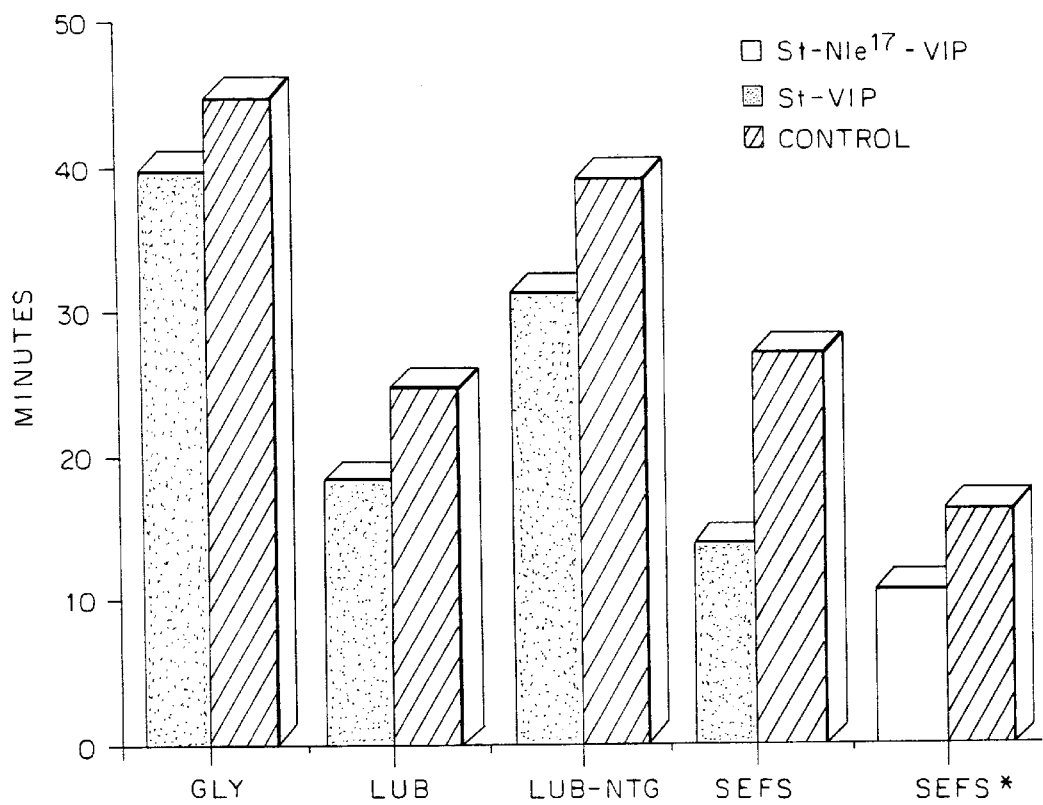
FIG. 2 shows the latency to first cup (min) of animals topically administered with various vehicles containing St-Nle$^{17}$-VIP, St-VIP and vehicle alone (control)

FIG. 2 shows the latency to first cup of animals administered with different vehicles comprising St-VIP, St-Nle$^{17}$-VIP and vehicle alone (control) wherein again as in FIG. 1, the shortest latency to the first cup is observed following transdermal application of St-Nle$^{17}$-VIP in Sefsol 318™ (lane 5, SEFS*, shortest latency=10 minutes).

Number of E2 (St-Nle$^{17}$-VIP)

Figure 3:
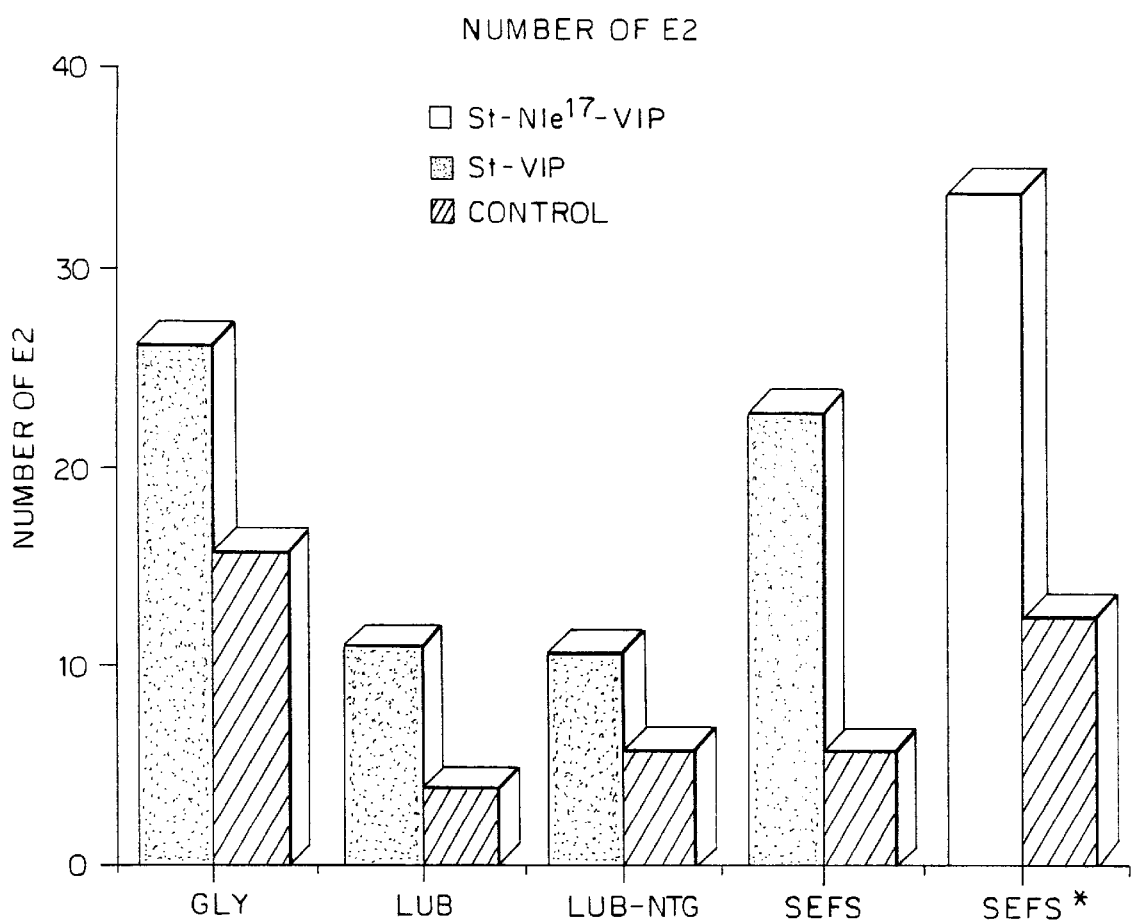
FIG. 3 shows the number of E2 of animals topically administered with various vehicles containing St-Nle$^{17}$-VIP, St-VIP and vehicle alone (control)
Figure 4:
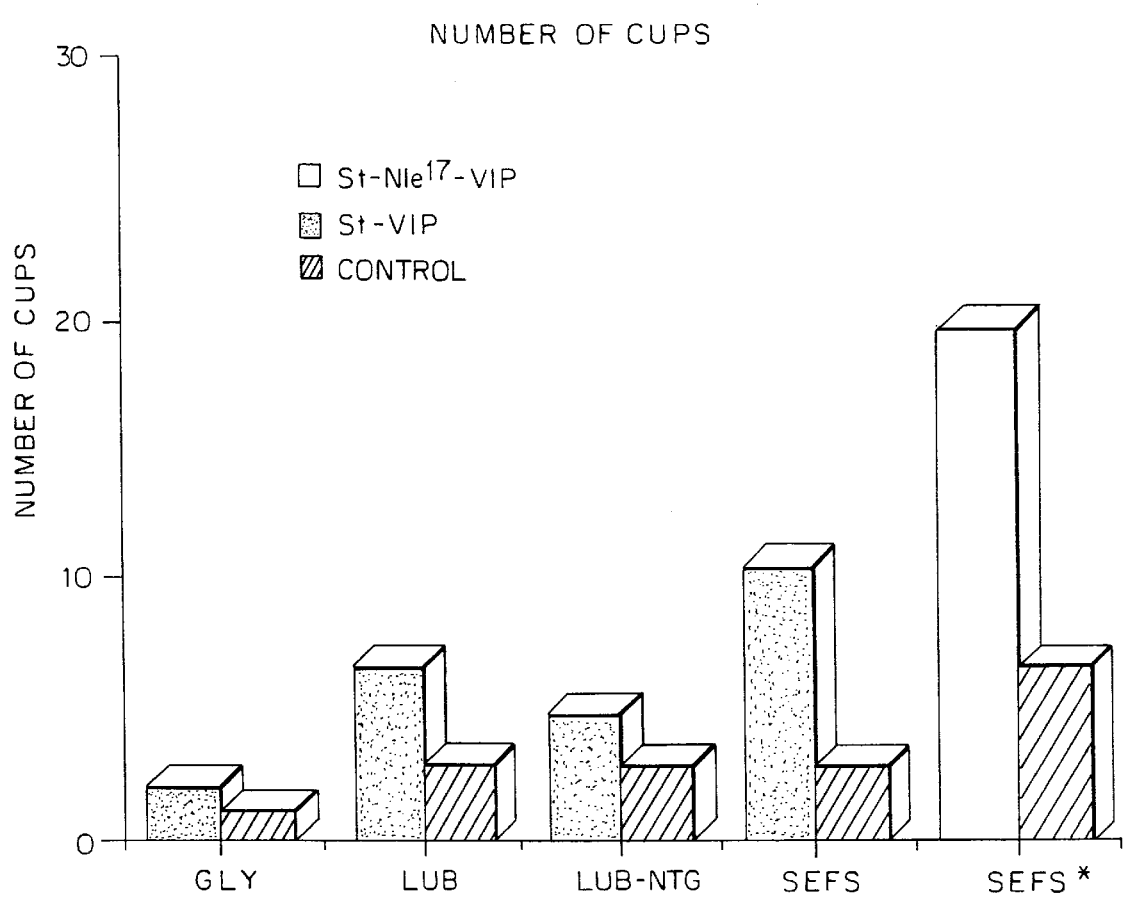
FIG. 4 shows the number of cups of animals topically administered with various vehicles containing St-Nle$^{17}$-VIP, St-VIP and vehicle alone (control)
Figure 5:
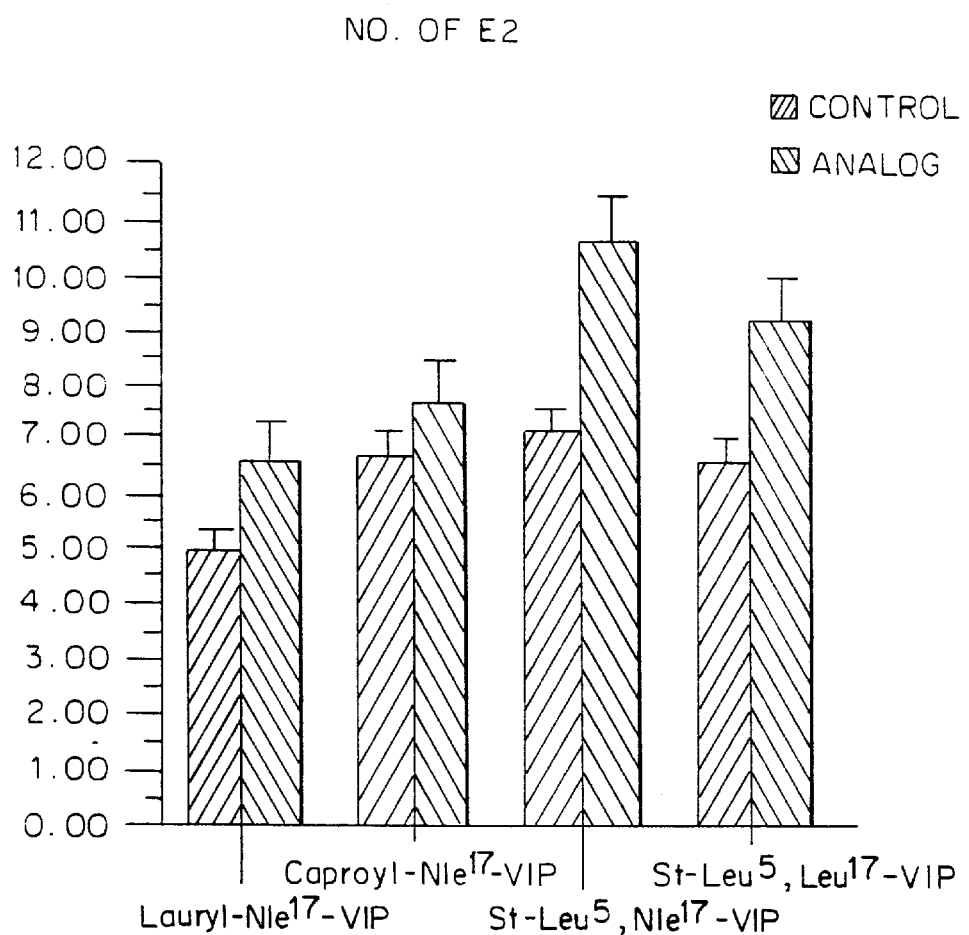
FIG. 5 shows the number of E2 of animals administered with: lauryl-Nle$^{17}$-VIP; caproyl-Nle$^{17}$-VIP, St-Leu$^5$-Leu$^{17}$-VIP and St-Leu$^5$-Nle$^{17}$-VIP as compared to control.

FIG. 3 shows the latency to first cup of animals administered with different vehicles comprising St-VIP, St-Nle$^{17}$-VIP and vehicle alone (control) wherein in agreement with FIGS. 1 and 2, the highest number of E2 is observed when treating the rats with the composition of St-$Nle^{17}$-VIP in Sefsol 318™ (SEFS* in lane 5). The number of E2 using this composition is much higher than the number of E2 observed using a composition of stearoyl-VIP and Sefsol 318™ (SEFS* in lane 4). These results clearly demonstrate the superiority of the structurally modified VIP conjugate (34 vs 24 of E2 during the test period).

Number of Cups (St-$Nle^{17}$-VIP)

FIG. 4 shows the number of cups of animals administered with different vehicles comprising St-VIP, St-$Nle^{17}$-VIP and vehicle alone (control) wherein in agreement with the above figures the highest number of cups is also observed for the composition containing St-$Nle^{17}$-VIP in Sefsol 318™ (SEFS* in lane 5). The number of cups using Sefsol 318™ in combination with St-VIP (SEFS* in lane 4) and St-$Nle^{17}$-VIP (SEFS* in lane 5) were 12 and 20, respectively.

Number of E2—using various modified conjugates

The number of E2 obtained when using modified VIPs is given in FIG. 5. Lauroyl-$Nle^{17}$-VIP, caproyl-$Nle^{17}$-VIP, St-$Leu^5Leu^5$-VIP and St-$Leu^5$, $Nle^{17}$-VIP were topically administered to animals and the results were compared to results obtained when using vehicle alone (control). The highest number of E2 using these compositions was obtained while using St-$Leu^5$-$Leu^{17}$-VIP as the active ingredient in the ointment, although all the other modified VIPs tested caused a significantly higher number of E2 than control.

Number of Cups—using various modified conjugates

The number of cups obtained when using modified VIPs is given in FIG. 6. Lauroyl-$Nle^{17}$-VIP, caproyl-$Nle^{17}$-VIP, St-$Leu^5Leu^5$-VIP and St-$Leu^5$, $Nle^{17}$-VIP were topically administered to animals and the results were compared to results obtained when using vehicle alone (control). In agreement with FIG. 5, the highest number of cups was observed when treating the rats with the compositions containing St-$Leu^5$-$Leu^{17}$-VIP, although all other modified VIPs tested caused a significantly higher number of cups than control.

From the above results, it is clear that modifications of conjugates of VIP to lipophilic moieties, (mainly stearoyl-VIP), for example in positions 5 and 17, increases the effectiveness of the compound in stimulating sexual activity.

A second conclusion that emerges is that Sefsol 318™ seems to be a suitable carrier for the transdermal delivery of stearoyl-VIP as well as for stearoyl-$Nle^{17}$-VIP. According to all the four parameters tested, the transdermal application of a composition containing Sefsol 318™ with stearoyl-$Nle^{17}$-VIP is more efficient than a composition of Sefsol 318™ and stearoyl-VIP.

EXAMPLE 9

Comparisons among Various Conjugates of the Invention

Three positions in VIP were chosen for amino acid substitutions being amino acid residues in positions 5, 17 and 19. All peptides tested bear a lipophilic moiety at their N-terminus ($R^1$) and/or C-terminus ($R^2$). Whenever $R^2$ is not indicated the peptide conjugate tested is amidated at its C-terminal.

The following table summarizes the effects of the tested conjugates on the number of cups and E2 (*indicating a substitution as compared to native VIP):

TABLE 3

Biological effects of conjugates

| $R_1$ | 5 | 17 | 19 | $R_2$ | No. of cups | No. of E2 | Activity |
|---|---|---|---|---|---|---|---|
| Prop | Val | Nle* | Val | | 45.8 ± 10 | 13.2 ± 4.6 | +++ |
| St | Val | Nle* | Val | | 27 | 9 | ++ |
| Tric | Val | Nle* | Val | | 36.75 ± 2.95 | 12 ± 0.4 | +++ |
| | Val | Nle* | Val | Caproylaminolauryl amide | 42 ± 4.8 | 12.5 ± 1.2 | +++ |
| Aca | Val | Nle* | Val | Carboxyamidolauroyl | 32 ± 3.1 | 11.75 ± 0.85 | ++ |
| St | Leu* | Nle* | Val | | 22.75 ± 2.35 | 9.25 ± 0.25 | + |
| St | Val | Ile* | Val | | 32 ± 0 | 115 ± 0.5 | ++ |
| St | Val | Trp* | Val | | 30 ± 6 | 12 ± 1.0 | ++ |
| St | Val | Abu* | Val | | 23.25 ± 5.1 | 9.25 ± 1.3 | + |
| St | Val | Ala* | Val | | 24.5 ± 0.5 | 10 ± 0 | + |
| St | Val | dNle* | Val | | 27 ± 5.1 | 10 ± 13 | + |
| St | Ala* | Nle* | Val | | 36.5 ± 1.5 | 14 ± 1.0 | ++ |
| St | Leu* | Met | Leu* | | 29 ± 6 | 10.5 ± 1.5 | ++ |
| St | Nle* | Nle* | Nle* | | 21.5 ± 3.5 | 9 ± 1 | + |
| St | Gly* | Met | Val | | 30.3 ± 5.1 | 11.2 ± 1.1 | ++ |
| St | Nle* | Pbe* | Val | | 23.5 ± 1.3 | 9.5 ± 0.3 | + |
| | | | Control vehicle | | 192 ± 1.5 | 8.4 ± 0.75 | |

Prop = $CH_3$—$CH_2$—CO—

Caproyl aminolauroyl amide (C12) = —$(CH_2)_5$CO—NH—$(CH_2)_{11}$$CONH_2$

Tric = $CH_3$—$(CH_2)_{21}$—CO—

Abu = α-butylic amino acid

* = modified amino acid as compared to native VIP.

These results demonstrate that replacement of amino acids of a conjugate of VIP and a lipophilic moiety in positions 5, 17 and/or 19 or a combination of such replacement results in enhancement of sexual responses. These results further indicate that the lipophilic moiety can be present at the N- or C-terminal or at both terminals.

Substitution of asparagine in position 28 with beta-Ala ($NH_2$—$CH_2$—$CH_2$—COOH) resulted in loss of activity (data not shown) indicating that change in other amino acid residues beyond those in positions 5, 17 and 19 may be crucial.

EXAMPLE 10

Skin Penetration Experiment and Body Distribution

These experiments were divided into two groups. In the first group of experiments we performed a time course of the distribution of radioactively labelled stearoyl-Nle$^{17}$-VIP (in Sefsol 318™), applied transdermally to the penis of the animals, in various organs of the body. In the second group of experiments we compared the penetration of radioactively labelled VIP, Nle$^{17}$-VIP St-VIP and St-Nle$^{17}$-VIP with Sefsol 318™ following transdermal application. Two to four animals were used for each data point. The derivatives were labelled with 1251 using the chloramine-T based method$^{(14)}$.

In the first group of experiments, stearoyl-Nle$^{17}$-VIP was radioactively labelled with $I^{125}$. Each animal received 2.2 million CPM, in 6µl of the radioactive material+ 26µl ointment (ointment No. 4 in Example 5). Two animals were used for each time point in two independent experiments. To avoid oral absorbance, the animal mouth was sealed. At indicated times following topical application, animals were sacrificed and duplicate tissue samples were removed, weighed and counted in a gamma counter. Tissues measured were: lungs (LU), heart (HE), kidneys (KI), liver (Li) and intestine (IN).

The results shown in FIG. 7 clearly demonstrate peak deliveries between 15–60 minutes after administration and disappearance of St-Nle$^{17}$-VIP after 2.5 hours.

In the second group of experiments compositions of Sefsol 318™ and VIP, St-VIP, Nle$^{17}$-VIP and St-Nle$^{17}$-VIP were prepared. The experiments were performed as in FIG. 7 with the only difference that each animal received a 2.4 million CPM, 2–4 animals were utilized for each variable. Animals were sacrificed 30 minutes after the application of the drug.

The results shown in FIG. 8 are in agreement with the results of the sexual reflexes paradigm, as the highest concentrations were found for St-Nle$^{17}$-VIP compositions, which is the most efficient drug.

As in the penile reflexes experiments, these last experiments also show the superiority of St-Nle$^{17}$-VIP over the other derivatives, in terms of skin penetration and tissue distribution.

EXAMPLE 11

Toxicology Studies

To assess the degree of toxicity and possible side effects of stearoyl-Nle$^{17}$-VIP, two types of studies were performed:
1. acute toxicology studies; 2. repeated dose toxicity studies.
A. Topical Use
Treatment Groups
Method The repeated dose toxicity of stearoyl-Nle$^{17}$-VIP administered topically was investigated in 80 SPF (Specified pathogen free) rats divided into 4 groups of ten male and ten female Sprague Dawley (S.D.) strain rats purchased from Harlan, Olac, England.
Test group constitution:
Group 1: 7 µg stearoyl-Nle$^{17}$-VIP+vehicle (1× dose)
  Females: Animal numbers 1 to 10
  Males: Animal numbers 41 to 50
Group 2: 700 µg stearoyl-Nle$^{17}$-VIP+vehicle (100× dose)
  Females: Animal numbers 11 to 20
  Males: Animal numbers 51 to 60
Group 3: 3500 µg stearoyl-Nle$^{17}$-VIP+vehicle (500× dose)
  Females: Animal numbers 21 to 30
  Males: Animal Numbers 61 to 70
Group 4: Vehicle only (5% Sefsol+20% isopropanol)
  Females: Animal numbers 31 to 40
  Males: Animal numbers 71 to 80
Results
Mortality No mortality associated with drug application was noted throughout the study. Only one death took place of a male from the low dose group (Group 1M, Animal number 47), Death occurred due to a massive abdominal hemorrhage caused by a nephroblastoma,
Adverse Effects No dose related adverse effects were detected throughout the study period. Clinical signs seen were: penile oedema and erythema, yellow staining of the penis, bleeding from the preputium or vagina, abscessation in the abdominal area close to the sex organs. Most of these signs were seen transiently. One male rate developed transient diarrhea which disappeared after a week. Penile oedema, erythema and staining were seen only in the treatment groups and not in the control, however without a dose relationship.

The incidence and severity of the clinical signs were not dose related and are considered to probably be related to the repeated handling of the rats.
Body Weight Gain and Food Consumption No significant differences were detected for either the male and female rats for body weight gain or food consumption throughout the treatment period.
Clinical Pathology No dose related or sex related biologically meaningful treatment effects were detected for either the hematology or clinical chemistry parameters tested.
Organ Weight Analysis No treatment related differences were noted between any of the treatment groups as compared to the control group, for either the male or female animals.
Conclusion Under the conditions of this study, daily topical application of stearoyl-Nle$^{17}$-VIP for 13 weeks did not cause any serious adverse effects at any of the dosages tested. Minor changes which were not dose related tended to disappear despite the continuation of treatment. The clinical signs noted are considered probably to be related to the repeated daily handling of the rats and their genitalia.
B. Intravenous use
Treatment Groups
Method The single dose toxicity of stearoyl-Nle$^{17}$-VIP injected intravenously, into the tail vein, was investigated in 4 groups of six male and six female rates [Sprague Dawley (S.D.) strain, purchased from Levinstein, Yokneam, Israel).

| Test Groups constitution: |  |
|---|---|
| 1. Saline |  |
| 2. Vehicle (Sefsol 5% + isopropanol 50%) |  |
| 3. Stearoyl-Nle$^{17}$-VIP | 7 μg/rat + vehicle |
| 4. Stearyol-Nle$^{17}$-VIP | 7,000 μg/rat + vehicle |

Results
Mortality

Seven rats (3 male and 4 female out of 12) died in Group 4, within 3 hours after administration One rat died in Group 2 within 5–24 hours after administration. No mortality occurred in Groups 1 and 3, Under the conditions of this study, the acute intravenous median lethal dose (LD50) of stearoyl-Nle$^{17}$-VIP+vehicle was estimated to be 7,000 μg/male rat, and due to the higher mortality in females, it was estimated to be less that 7,000μg for the combined males and females.

Necrotic Reaction

Necrotic reaction was observed at the site of injection (tail skin) in all groups receiving the vehicle and vehicle+drug: 55% of the animals in Group 2. 58% of the animals in Group 3, and all the animals in Group 4.

Side Effects

No other side effects were observed in surviving rats of all groups.

Body Weight Gain and Food Consumption

Most of the surviving rats displayed normal body weight gain and showed normal food consumption during the two weeks study period. Statistical analysis (ANOVA) revealed differences between animals receiving the drug (increased weight gain) and the control group (vehicle), Following intravenous injection a weight loss was sometimes observed which was recovered later during the experiment.

Conclusion

Under the conditions of this study, the acute intravenous median lethal dose (LD50) of stearoyl-Nle$^{17}$-VIP+vehicle was estimated to be 7,000 μg/male rat, and due to the higher mortality in females, it was estimated to be less that 7,000 μg for the combined males and females.

C. Hypersensitivity Test

Skin sensitization in guinea pigs is a predictive animal test to determine the potential of substances to induce delayed hypersensitivity in humans.

A study was designed to assess the degree of skin sensitization resulting from intradermal Freund's complete adjuvant and patch application of stearoyl-Nle$^{17}$-VIP. Due to the nature of the compound and its vehicle it was decided to use the "Adjuvant and Patch Test".

The logic of the dose design was as follows: pharmacological experimentation has shown that the biologically active dose is 7 μg per rat. The dose of 1000× the biologically active dose was chosen for this experiment.

Method
Test Material

Name: Stearoyl-Nle$^{17}$-VIP (prepared and purified as described in Example 1)

Appearance: Powder

Stability Powder: (for a year)

Refrigerated in an solubilized form (for at least six weeks)

Vehicle Sefsol (purchased from Sigma Co.)+Isopropanol

Preparation of test material +vehicle per animal;

7 mg stearoyl-Nle$^{17}$-VIP+250 μl 10% Sefsol+250 μl 40% isopropanol [500 μl/animals=1000× dose].

The material was mixed on the same days 3 hours before dosing.

Positive control substance

1% 1-chloro-2,4-dinitrobenzene in dibutylphthalate.

Results

Both stearoyl-Nle$^{17}$-VIP dissolved in vehicle and the vehicle alone did not cause a hypersensitivity response, while positive control application of 1-chloro-2,4-dinitrobenzene caused prominent hypersensitivity reaction in guinea pigs.

This study showed that both stearoyl-Nle$^{17}$-VIP and the vehicle alone have no skin sensitization properties

We claim:

1. A conjugate of a lipophilic moiety and a modified vasoactive intestinal peptide (VIP), selected from the group consisting of stearoyl-tryptophan$^{17}$-VIP, stearoyl-alanine$^5$-norleucine$^{17}$-VIP and stearoyl-glycine$^5$-VIP.

2. A conjugate according to claim 1, being stearoyl-tryptophan$^7$-VIP.

3. A conjugate according to claim 1, being stearoyl-alanine$^5$-norleucine$^{17}$-VIP.

4. A conjugate according to claim 1, being stearoyl-glycine$^5$-VIP.

5. A conjugate of a (1) lipophilic moiety and (2) a modified vasoactive intestinal peptide, said modified vasoactive intestinal peptide (2) being selected from the group consisting of norleucine$^{17}$-VIP, leucine$^5$-leucine$^{17}$-VIP, leucine$^5$-norleucine$^{17}$-VIP, and isoleucine$^{17}$-VIP.

6. A conjugate according to claim 5 selected from the group consisting of stearoyl-norleucine$^{17}$-VIP, caproyl-norleucine$^{17}$-VIP, lauroyl-norleucine$^{17}$-VIP, stearoyl-leucine$^5$-leucine$^{17}$-VIP, stearoyl-leucine$^5$, norleucine$^{17}$-VIP, propanoyl-norleucine$^{17}$-VIP, tricosanoyl-norleucine$^{17}$-VIP, norleucine$^{17}$-VIP-caproylaminolauroyl amide, aminocaproyl-norleucine$^{17}$-VIP-lauroyl amide and stearoyl-isoleucine$^{17}$-VIP.

7. A conjugate according to claim 6, being stearoyl-norleucine$^{17}$-VIP.

8. A conjugate according to claim 6, being caproyl-norleucine$^{17}$-VIP.

9. A conjugate according to claim 6, being lauroyl-norleucine$^{17}$-VIP.

10. A conjugate according to claim 2 which is stearoyl-leucine$^5$-leucine$^{17}$-VIP or stearoyl-leucine$^5$-norleucine$^{17}$-VIP.

11. A conjugate according to claim 10, being stearoyl-leucine$^5$-leucine$^{17}$-VIP.

12. A conjugate according to claim 10, being stearoyl-leucine$^5$, norleucine$^7$-VIP.

13. A topical pharmaceutical composition for transdermal application containing as an active ingredient a conjugate according to claim 5, in combination with a pharmaceutically acceptable topical carrier.

14. A pharmaceutical composition according to claim 13, wherein said pharmaceutically acceptable topical carrier comprises glycerol monocaprylate.

15. A pharmaceutical composition for transdermal application containing as an active ingredient a conjugate according to claim 6, in combination with a pharmaceutically acceptable carrier selected from the group consisting of glycerine, olive oil, lubricants, nitroglycerine, glyceryl monocaprylate, propylene glycol didecanoate, propylene glycol dicaprylate, glyceryl tricaprylate and sorbitan monocaprylate, and mixtures thereof.

16. A pharmaceutical composition according to claim 14, wherein said active ingredient is stearoyl-norleucine$^{17}$-VIP and said pharmaceutically acceptable carrier is glyceryl monocaprylate.

17. A method of treating male impotence comprising transdermally applying the composition of claim 13, to a penis of a male patient in need of said treatment.

18. A method of treating male impotence comprising transdermally applying the conjugate of claim 5, to a penis of a male patient in need of said treatment.

19. A method of treating male impotence comprising transdermally applying the composition of claim 16, to a penis of a male patient in need of said treatment.

* * * * *

SEQUENCE LISTING

```
<160> NUMBER OF SEQ ID NOS: 2

<210> SEQ ID NO 1
<211> LENGTH: 28
<212> TYPE: PRT
<213> ORGANISM: Human

<400> SEQUENCE: 1

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
                20                  25

<210> SEQ ID NO 2
<211> LENGTH: 28
<212> TYPE: PRT
<213> ORGANISM: Human
<220> FEATURE:
<223> OTHER INFORMATION: Xaa at position 5, Xaa at position 17, and Xaa
      at position 19 are the same or different provided
      that when in full sequence both Xaa at 5 and 19
      are val and Xaa at 17 is not methionine

<400> SEQUENCE: 2
```

```
His Ser Asp Ala Xaa Phe Thr Asp Asn Tyr Thr Arg Leu Arg Lys Gln
 1           5                   10                  15

Xaa Ala Xaa Lys Lys Tyr Leu Asn Ser Ile Leu Asn
            20                  25
```